United States Patent [19]

Kaneko et al.

[11] Patent Number: 5,075,226
[45] Date of Patent: Dec. 24, 1991

[54] METHD FOR THE FERMENTATIVE PRODUCTION OF DIACETYL AND ACETOIN USING LACTIC ACID BACTERIUM

[75] Inventors: Tsutomu Kaneko; Masahiro Takahashi, both of Tokyo; Hideki Suzuki, Tokorozawa, all of Japan

[73] Assignee: 501 Meiji Milk Products Co., Ltd., Tokyo, Japan

[21] Appl. No.: 581,601

[22] Filed: Sep. 12, 1990

[30] Foreign Application Priority Data

Nov. 28, 1989 [JP] Japan .................................. 1-306405
Mar. 29, 1990 [JP] Japan .................................... 2-78626

[51] Int. Cl.$^5$ ......................... C12P 7/26; C12R 1/225; C12R 1/46; A23C 19/032
[52] U.S. Cl. ......................................... 435/148; 426/7; 426/18; 426/34; 426/43; 435/853; 435/885
[58] Field of Search ....................... 435/148, 885, 853; 426/18, 7, 34, 43

[56] References Cited

U.S. PATENT DOCUMENTS 4,304,862 12/1981 Troller ................................ 435/138

OTHER PUBLICATIONS

Biotech Abs. AN-85-02151 Orberg et al. AEMIDF "Appl. Environ. Mibrobiol" (1984) 48,6,1129-33.
Chem. Abs. AN13-168741 (19) Kaneko et al. AEMIDF "Appl. Environ. Microbiol" (1990) V56 (9) p. 2644-2649.
Collins, E. B. "Biosynthesis of Flavor Compounds by Microorganisms." *Journal of Dairy Science* 55/7: 1022-1028 (1972).
Kaneko, T. et al., "Diacetyl Formation and Degradation by *Streptococcus lactis* subsp. *diacetylactis* 3022." *Agric. Biol. Chem.* 50/10: 2639-2641 (1986).
Drinan, D. F. et al., "Citric Acid Metabolism in Hetero- and Homofermentative Lactic Acid Bacteria." *Applied and Environmental Microbiology* 31/4: 481-86 (1976).
Pack, M. Y. et al., "Effect of Temperature on Growth and Diacetyl Production by Aroma Bacteria in Single- and Mixed-Strain Lactic Cultures." *J. Dairy Science* 51/3: 339-344 (1968).
Kaneko, T. et al., "The Effects of Metal on Diacetyl Production by *Streptococcus lactis* subsp. *diacetylactis* 3022." *Agric. Biol. Chem.* 51/9: 2315-2320 (1987).
Benito De Cardenas, I. L. et al., "Diacetyl and Acetoin Production by Lactobacilli in a Synthetic medium." *Milchwissenschaft* 38/4: 218-220 (1983).
Oberman, H. et al., "Production of Diacetyl and Acetoin by Lactic Acid Bacteria." *Die Nahrung* 26: 615-623 (1982).

Primary Examiner—Herbert J. Lilling
Attorney, Agent, or Firm—Pennie & Edmonds

[57] ABSTRACT

A method for fermenting diacetyl and acetoin with a lactic acid bacterium by adding one or more additives selected from ferroporphyrin, heme protein, an animal tissue containing ferroporphyrin and blood and metal salts to a culture substrate containing a sugar source which a lactic acid bacterium can use, inoculating the lactic acid bacterium into the substrate and then aerobically culturing the bacterium with shaking or under aeration. A culture solution containing high concentrations of diacetyl and acetoin obtained by the present invention or its diacetyl concentrate is used to increase or improve the flavor of foods such as oils and fats, e.g., butter, margarine, cheeses, shortening, etc., confectionery, creams and the like.

5 Claims, 1 Drawing Sheet

METHOD FOR THE FERMENTATIVE PRODUCTION OF DIACETYL AND ACETOIN USING LACTIC ACID BACTERIUM

BACKGROUND OF THE INVENTION

Industrial Applicability

This invention relates to a method for the fermentative production of diacetyl and acetoin using a lactic acid bacterium. In particular, it relates to a method for the fermentative production of diacetyl and acetoin using a lactic acid bacterium by culturing said bacterium in a culture medium containing a sugar source which said bacterium can utilize.

Diacetyl and acetoin are principal flavoring components produced by a lactic acid bacterium.

Prior Art

It is known that diacetyl and acetoin are flavoring components produced by a lactic acid bacterium capable of utilizing citric acid, for example, (Cit+) *Lactococccus lactis* subsp. lactis (*Streptococcus lactis* subsp. *diacetylactis*), *Leuconostoc mesenteroides* subsp. *cremoris* and the like, using citric acid as a substrate. Therefore, the productivity of diacetyl and acetoin by a lactic acid bacterium is closely related to the metabolic activity of citric acid and its metabolites. Most of the previously reported methods for increasing the yield of diacetyl and acetoin depend on the premise that citric acid is a precursor of these flavoring components.

For example, these flavoring components have been produced with the addition of a metal salt to a culture medium so as to increase the citrate-metabolizing activity of the lactic acid bacterium, or by culturing the lactic acid bacterium in the presence of citric acid for a certain period of time, then adding cirtic acid and a metal salt, and culturing again for several hours [Agric. Biol. Chem., 51, 2315 (1987)], or by culturing, at a lower temperature or at a lower pH so as to reduce the diacetyl reductase activity [J. Dairy Sci., 51, 339 (1968)], or by adding citric acid or pyruvic acid to a medium as a precursor of diacetyl and acetoin [Die Nahrung,26, 615 (1982) and Milchwissenschaft, 38, 218 (1976)], etc. However, it has been found that a lactic acid bacterium contains diacetyl reductase and diacetyl formed is immediately converted to acetoin by the action of this enzyme [J. Dairy Sci., 55, 1022 (1972)]. Acetoin is a flavoring component giving a flavor similar to that of diacetyl. However, the flavor of acetoin is considerably weaker as compared with that of diacetyl, so that it is necessary to prevent the conversion of diacetyl formed to acetoin in order to increase the flavor strength. This object can also be attained by oxidizing acetoin, when formed in large quantity, to diacetyl.

On the other hand, the production of diacetyl reductase and the activity thereof are considered to decrease when citric acid is present in a medium. Therefore, as soon as citric acid is consumed, conversion of diacetyl to acetoin occurs rapidly.

It has been known that, when (Cit+) *Lactococcus lactis* subsp. *lactis* 3022, a strain of lactic acid bacteria, is subjected to static culture in MRS medium at 30° C. for 8 hours, the decrease in the amount of the diacetyl formed immediately occurs as soon as citric acid in the medium is almost used up, to lower the yield of diacetyl [Agric. Biol. Chem., 50, 2639 (1986)]. Such conversion of diacetyl to acetoin during culturing may bring about some difficulties to a reliable production of diacetyl. In addition, the amount of diacetyl formed by culturing a lactic acid bacterium in a medium containing skim milk powder containing or the like is generally as low as 2 to 10 ppm.

That is, it is a significant problem of the prior art to prevent the conversion of diacetyl to acetoin. On the other hand, pyruvic acid as a direct precursor of diacetyl and acetoin is formed by the metabolism of carbohydrates such as glucose and the like, in addition to the metabolism of citric acid. It is generally assumed that a lactic acid bacterium does not produce diacetyl in the absence of citric acid [Appl. Environ. Microbiol., 31, 481 (1976)]. However, if diacetyl and acetoin can be produced by the metabolism of carbohydrates alone, the addition of citric acid becomes unnecessary and the production costs can be reduced, thus industrially much advantageous.

SUMMARY OF THE INVENTION

The object of this invention is to provide a method for the fermentative and reliable production of diacetyl and acetoin in high yield, by culturing a lactic acid bacterium in a medium containing a sugar source which said bacterium can utilize.

The inventors have surprisingly found that, when (Cit+) *Lactococcus lactis* subsp. *lactis* 3022 (FERM BP-2805) was shaking cultured in MRS medium, the following results could be obtained in comparison with the static culture:

(1) The diacetyl-forming (diacetyl synthase) activity increased approx. 5 times (Table 1);

(2) The amount of glucose consumed increased, whereas the amount of lactic acid formed decreased (Table 2);

(3) Even after 8 hours of culture when citiric acid in the medium was completely consumed, the amount of accumulated diacetyl increased and no decrease in diacetyl amount could be observed; therefore, diacetyl could reliably be produced (FIG. 1); and (4) Even in MRS medium without the addition of citric acid, the formation of diacetyl and acetoin occured (Table 3).

These results suggest that, because the diacetyl-forming activity of a lactic acid bacterium increases when aerobically cultured with shaking, diacetyl and acetoin can also be formed from pyruvic acid which is produced from glucose, not only from citric acid.

In addition to the above findings, the present inventors have further found that substantially all the added sugar source can be metabolized into diacetyl and acetoin, that is, diacetyl and acetoin can be fermentatively produced when a lactic acid bacterium is cultured aerobically by shaking or aerating the cuture medium containing at least one additive selected from iron porphyrin, heme protein, an animal tissue containing iron porphyrin, and blood, and also containing one or more metal salts.

Thus, the present invention relates to a method for the fermentative production of diacetyl and acetoin, which comprises culturing a lactic acid bacterium in a culture medium containing a sugar source which said lactic acid bacterium can utilize, with shaking or under aeration in the presence of one or more additives selected from iron porphyrin, heme protein, an animal tissue containing iron porphyrin, and blood and also in the presence of one or more metal salts.

Figure 1:
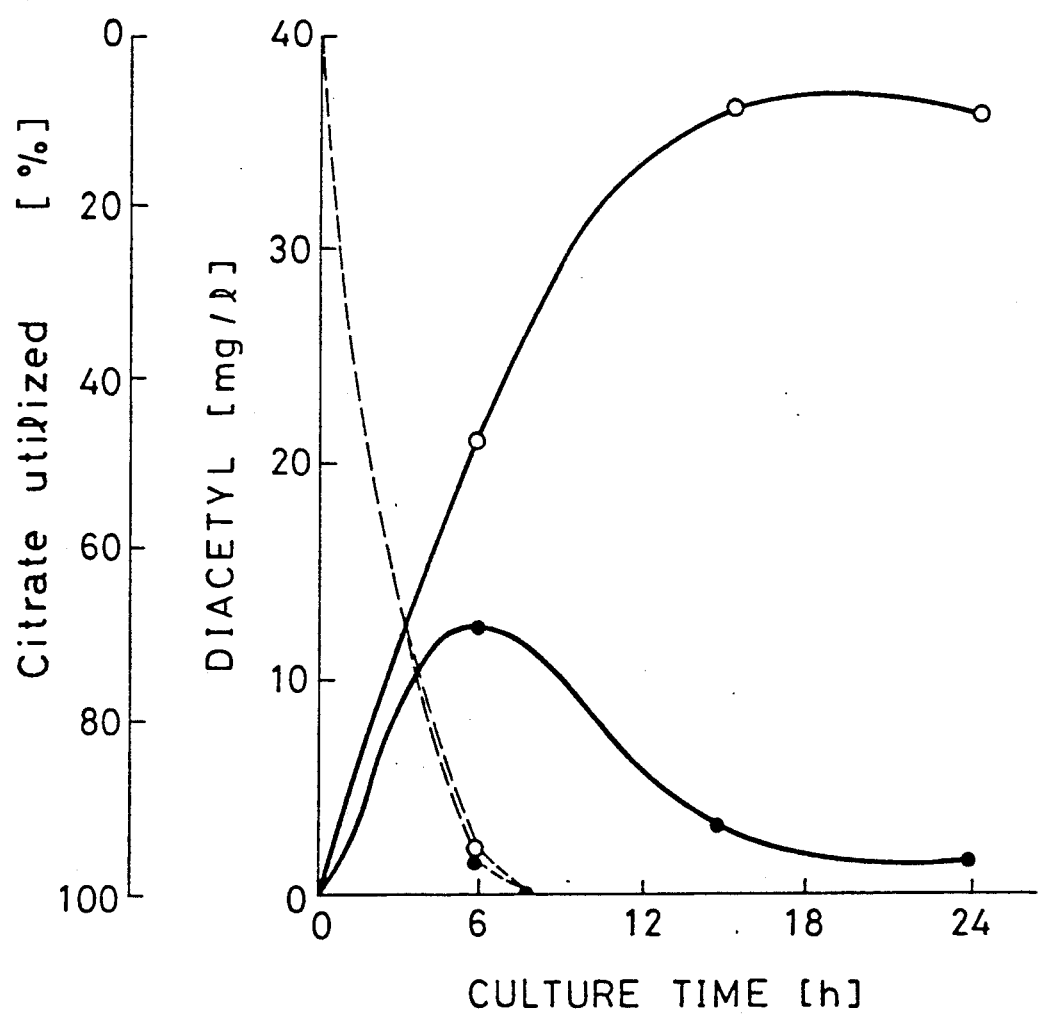
FIG. 1 shows the relationship between the amount of diacetyl formed and that of citric acid consumed, obtained by inoculating 1 ml of a preculture of (Cit+) *Lactococcus lactis* subsp. *lactis* 3022 into a Sakaguchi flask (containing 100 ml of MRS medium) and conducting static culture (●) at 30° C. or shaking culture (○) at 120 strokes/min.. The solid line (—) indicates the amount of diacetyl formed and the dashed line (---) indicates the amount of citric acid consumed.

Any carbon source may be used in the present invention, so far as it can be used by the lactic acid bacterium. Glucose, lactose, etc. are preferred.

Example of iron porphyrin, which may be used in the sense inclusive of heme protein, are heme, hemin and hematin.

Examples of heme protein which may be mentioned include cytochrome oxidase, cytochrome, catalase, peroxidase, hemoglobin, etc.

The amount of iron porphyrin, heme protein, an animal tissue containing iron porphyrin, and blood to be added ranges from 0.1 to 500 μM, preferably 0.5 to 5 μM, on the iron porphyrin basis.

As the metal salts, one or more of iron ion, copper ion and molybednum ion may be added in the form of inorganic or organic salts to a concentration of 0.01 to 10 mM in total.

As examples of the inorganic salts, chlorides, sulfides, etc. may be mentioned, and acetates, lactates, etc., may be mentioned as organic salts.

Although citric acid is not an essential component, it may also be added to the medium. When citric acid is added to the medium, the production of diacetyl and acetoin in such medium becomes somewhat higher as compared with those without citric acid.

The above-mentioned iron porphyrin, heme protein, an animal tissue containing iron prophyrin or blood, and metal salts may be added to a medium after heat-sterilizing the medium or simultaneously with the other medium components prior to heat-sterilization. Particularly, in case of heme protein such as hemoglobin, cytochrome oxidase, catalase and peroxidase, the diacetyl- and acetoin-productivity of a lactic acid bacterium increases due to the presence of iron porphyrin contained in said protein and not by their specific enzymatic actions. Therefore, it is also possible to carry out the present process by adding animal blood, animal tissues, e.g., liver, kidney, etc. or their extracts containing iron porphyrin which is less expensive than the aforementioned heme protein to a culture medium in a concentration of 0.1 μM or more based on iron porphyrin, inoculating with a lactic acid bacterium and then aerobically culturing the bacterium with shaking or under aeration.

Any lactic acid bacterium may be used in the present invention as far as it is capable of producing diacetyl and acetoin irrespective of their ability of utilizing citric acid. However, it is preferred to use a microorganism belonging to the genera *Lactobacillus*, *Lactococcus* (formerly the genus *Streptococcus*) and *Leuconostoc*. Examples of such microorganisms are as follows:
*Streptococcus lactis* subsp. *diacetylactis* ATCC 11007, *Lactobacillus casei* ATCC 334, *Leuconostoc cremoris* ATCC 19254, (Cit+) *Lactococcus lactis* subsp. *lactis* 3022 (FERM BP-2805) and *Lactobacillus casei* 2206 (FERM BP-2806).

*Lactococcus lactis* subsp. *lactis* 3022, accession number FERM BP-2805, and *Lactobacillus casei* 2206, accession number FERM BP-2806 have each been deposited at the Fermentation Research Institute, Agency of Industrial Science and Technology, Ministry of International Trade and Industry, 1–3 Higashi 1-chome, Tsukuba-shi, Ibaraki-ken, Japan.

The lactic acid bacteria as mentioned above can be used alone or in combinations thereof.

Diacetyl-forming (Diacetyl Synthase) activity of shaking culture was compared with static culture by culturing (Cit+) *Lactococcus lactis* subsp. *lactis* 3022 in MRS medium, and the results are shown in Table 1.

TABLE 1

| Method | Time (h) | Diacetyl-forming (Diacetyl Synthase) Activity (mU/mg protein) |
|---|---|---|
| Static Culture (30°C.) | 6 | 1.4 |
|  | 15 | 3.3 |
| Shaking Culture (30° C.) | 6 | 7.0 |
|  | 15 | 17.6 |

In the above Table 1 and the following Tables 2 and 3, the amounts of diacetyl and acetoin and the diacetyl-forming activity were measured by head space gas chromatography according to a method of the present inventors [Agric. Biol. Chem., 50, 2639 (1986)]. Glucose, lactic acid and citric acid were measured enzymatically (Boehringer-Mannheim GMBH).

The composition of the MRS medium used was as follows:

peptone 10 g, lab-lemco powder 10 g, yeast extract 5 g, glucose 20 g, Tween 80 1 ml, $K_2HPO_4$ 2 g, sodium acetate 5 g, triammonium citrate 2 g, $MgSO_4 \cdot 7H_2O$ 200 mg, $MnSO_4 \cdot 4H_2O$ 50 mg and distilled water 1,000 ml; pH 6.5

The amount of glucose consumed and that of lactic acid formed in the shaking culture was compared with those of static culture by culturing (Cit+) *Lactococcus lactis* subsp. *lactis* 3022 in MRS Medium (24-hours at 30° C.). The results are shown in Table 2.

TABLE 2

| Method | Amount of Glucose Consumed (mM) | Amount of Lactic Acid Formed (mM) |
|---|---|---|
| Static Culture | 17.0 | 33.8 |
| Shaking Culture | 38.4 | 26.7 |

The amounts of diacetyl and acetoin formed in shaking culture were compared with those of static culture by culturing (Cit+) *Lactococcus lactis* subsp. *lactis* 3022 in a medium with or without citric acid (24-hours at 30° C.). The results are shown in Table 3.

TABLE 3

| Method | Addition of Citric Acid (as a citrate) | Amount of Diacetyl Formed (mg/l) | Amount of Acetoin Formed (mg/l) |
|---|---|---|---|
| Static Culture | Added | 1.0 | 200 |
|  | None | 0 | 0 |
| Shaking Culture | Added | 40 | 1,200 |
|  | None | 17 | <500 |

As stated above, substantially all of the sugar source added are converted to diacetyl and acetoin in the present process. Diacetyl and acetoin in the culture can be concentrated by distillation, etc. In addition, the acetoin formed can be converted to diacetyl by oxidation.

That is, the present invention enables the reliable production of diacetyl and acetoin in high concentration by using inexpensive sugar source as a substrate, without adding citric acid to the culture medium. The culture solution or a concentrate thereof can be used to increase or improve the flavor of foods such as butter, margarine, cheeses, shortening, confectionery, creams, etc., in only small amounts.

COMPARATIVE EXAMPLE

Procedure

To 100 ml each of citrate-free MRS medium [J. Appl. Bacteriol., 23, 130 (1960)] was added 300 μg of hemin, 1 ml of catalase (Sigma, 20,800 U/mg protein, 35 mg protein/ml), 0.5 g of bovine blood, 0.1 g of bovine liver, or 1.7 mg of $CuCl_2 \cdot 2H_2O$. After sterilizing at 121° C. for 10 minutes, 1 ml of a preculture of (Cit+)*Lactococcus lactis* subsp. *lactis* 3022 was inoculated thereinto and cultured at 30° C. for 48 hours with shaking at 120 strokes/min. The same procedure as above was also carried out with adding either a mixture of hemin and $CuCl_2 \cdot 2H_2O$ or a mixture of bovine liver and $CuCl_2 \cdot 2H_2O$. The amounts of diacetyl and acetoin formed were determined in each case and the results are shown in Table 4.

TABLE 4

Effects of Hemin, Catalase, Bovine Blood, Bovine Liver and Copper Ion on the formation of Diacetyl and Acetoin by (Cit+) *Lactococcus latis* subsp. *lactis* 3022

| Additive | Diacetyl mg/l | Acetoin mg/l |
|---|---|---|
| None | 17 | <200 |
| Hemin | 180 | 5,000 |
| Catalase | 175 | 5,200 |
| Bovine Blood | 180 | 5,500 |
| Bovine Liver | 190 | 5,000 |
| $CuCl_2 \cdot 2H_2O$ | 170 | 3,200 |
| Hemin + $CuCl_2 \cdot 2H_2O$ | 240 | 6,700 |
| Bovine Liver + $CuCl_2 \cdot 2H_2O$ | 330 | 8,400 |

It is evident from the above results that the diacetyl and acetoin production in the presence of the above additives is about ten-fold higher than that produced without any additives (see Table 4). Therefore, the addition of heme, heme protein, an animal tissue containing heme, or blood and the addition of metal salts are indispensable in order to fermentatively produce diacetyl and acetoin using a sugar as a substrate.

EXAMPLE

The present invention is further illustrated by the following Examples wherein all percentages are by weight unless otherwise stated.

EXAMPLE 1

0.1 mM $CuCl_2$ was added to 100 ml of citrate-free MRS medium, followed by heat-sterilization at 121° C. for 10 minutes. To this medium was added hemin (sterilized by filtration), which had been dissolved in 0.05 N NaOH, to a concentration of 5 μM. Then, (Cit+) *Lactococcus lactis* subsp. *lactis* OLS 3022 (FERM BP-2805) starter was inoculated into the medium thus prepared to a concentration of 1%, followed by culturing with shaking at 120 strokes/min. at 30° C. for 48 hours. The amounts of diacetyl and acetoin produced in the culture were determined and found to be 250 mg/l and 6,300 mg/l, respectively.

EXAMPLE 2

0.1 mM $FeCl_3$ and 100 mg of slurried bovine liver were added to 100 ml of citrate-free MRS medium, followed by heat-sterilization at 121° C. for 10 minutes. Then, this medium was inoculated with *Lactobacillus casei* ATCC 334 starter and (Cit+) *Lactococcus lactis* subsp. *lactis* OLS 3022 (FERM BP-2805) starter, both at a concentration of 1%, followed by culturing under aeration at 30° C. for 24 hours. The amounts of diacetyl and acetoin produced in the culture were 620 mg/l and 6,000 mg/l, respectively.

EXAMPLE 3

0.1 mM $CuCl_2$, 0.1 mM $FeCl_3$, 0.1 mM $Na_2MoO_4$ and a sufficient amount of catalase (Sigma, 20,800 U/mg protein) to give a concentration of 4,000 U/ml were added to 100 ml of MRS medium, followed by heat-sterilization at 121° C. for 10 minutes. Then, the resultant culture medium was inocoulated with *Leuconostoc cremoris* ATCC 19254 starter and (Cit+) *Lactococcus lactis* subsp. *lactis* OLS 3022 (FERM BP-2805) starter, both to a concentration of 1%, followed by culturing with shaking at 120 strokes/min. at 30° C. for 48 hours. The amounts of diacetyl and acetoin produced in the culture were 290 mg/l and 7,500 mg/l, respectively.

EXAMPLE 4

10 g skim milk powder, .01 g of yeast extract, 1.7 mg of $CuCl_2$, 90 ml of water and 50 mg of slurried bovine kidney were mixed, and heated at 95° C. for 10 minutes, followed by inoculation with (Cit+) *Lactococcus lactis* subsp. *lactis* OLS 3022 (FERM BP-2805) starter, to a concentration of 2%. Culturing was conducted under aeration at 30° C. for 48 hours. The amounts of diacetyl and acetoin produced in the culture were 230 mg/l and 5,900 mg/l, respectively.

EXAMPLE 5

0.1 mM $FeSO_4$ was added to a citrate-free MRS medium (sugar source, lactose), followed by heat-sterilization at 121° C. for 10 minutes. Then, hemin (sterilized by filtration) dissolved in 0.05 N NaOH was added to a concentration of 1 μM, followed by inoculation with *Lactobacillus casei* 2206 (FERM BP-2806) starter to a concentration of 1% and culturing with shaking at 125 strokes/min. at 35° C. for 24 hours. The amounts of diacetyl and acetoin produced in the culture were 900 mg/l and 2,000 mg/l, respectively.

What is claimed is:

1. A method for the fermentative production of diacetyl and acetoin, which comprises culturing a lactic acid bacterium selected from the group consisting of (Cit+) *Lactoccus lactis* subsp. *lactis* OLS 3022, which has accession no. FERM BP-2805, *Lactobacillus casei* 2206, which has accession no. FERM BP-2806, and mixtures thereof, in a culture medium containing a sugar source which said lactic acid bacterium can utilize, with shaking or under aeration in the presence of one or more additives selected from iron porphyrin, heme protein, an animal tissue containing iron porphyrin, and blood and also in the presence of one or more metal salts.

2. A method according to claim 1, wherein the lactic acid bacterium is *Lactobacillus casei* 2206 (FERM-2806).

3. A method according to claim 1, wherein the amount of each of the iron porphyrin, the heme protein, the animal tissue containing iron porphyrin and the blood is in the range of 0.1 to 500 μM on the iron porphyrin basis.

4. A method according to claim 1, wherein the metal salts are selected from the group consisting of iron, copper and molybdenum and are added in the form of inorganic salts or organic salts in total amount of 0.01 to 10 mM.

5. A method according to claim 1, wherein whe lactic acid bacterium is (Cit+)*Lactococcus lactis* subsp. *lactis* 3022 (FERM BP-2805).

* * * * *